(12) United States Patent
Kuwahara et al.

(10) Patent No.: US 11,357,454 B2
(45) Date of Patent: Jun. 14, 2022

(54) NURSING CARE RECIPIENT WATCHING SUPPORT SYSTEM

(71) Applicant: Fantastic Co., Ltd., Chiba (JP)

(72) Inventors: Ryota Kuwahara, Chiba (JP); Kaoru Kurebayashi, Chiba (JP); Takayoshi Shimbo, Chiba (JP); Mitsuo Shinohara, Chiba (JP)

(73) Assignee: FANTASTIC CO., LTD., Chiba (JP)

( * ) Notice: Subject to any disclaimer, the term of this patent is extended or adjusted under 35 U.S.C. 154(b) by 0 days.

(21) Appl. No.: 17/051,367

(22) PCT Filed: Apr. 25, 2019

(86) PCT No.: PCT/JP2019/017621
§ 371 (c)(1),
(2) Date: Oct. 28, 2020

(87) PCT Pub. No.: WO2019/212029
PCT Pub. Date: Nov. 7, 2019

(65) Prior Publication Data
US 2021/0045699 A1  Feb. 18, 2021

(30) Foreign Application Priority Data
May 1, 2018  (JP) .............................. JP2018-088173

(51) Int. Cl.
*G08B 21/00* (2006.01)
*A61B 5/00* (2006.01)
*A61B 5/11* (2006.01)

(52) U.S. Cl.
CPC .............. *A61B 5/747* (2013.01); *A61B 5/002* (2013.01); *A61B 5/0004* (2013.01);
(Continued)

(58) Field of Classification Search
CPC ....... A61B 5/747; A61B 5/0004; A61B 5/002; A61B 5/1113; A61B 5/742; A61B 5/746;
(Continued)

(56) References Cited

U.S. PATENT DOCUMENTS

| 6,624,754 | B1 * | 9/2003 | Hoffman | ............... G08B 21/023 340/573.1 |
| 8,810,388 | B2 * | 8/2014 | Jacobs | ................. G08B 21/043 340/521 |

(Continued)

FOREIGN PATENT DOCUMENTS

| JP | 2000-338261 A | 12/2000 |
| JP | 2004-133500 A | 4/2004 |

(Continued)

OTHER PUBLICATIONS

International Search Report for International Application No. PCT/JP2019/017621 dated Jul. 23, 2019 (2 sheets).

*Primary Examiner* — Anh V La
(74) *Attorney, Agent, or Firm* — Kratz, Quintos & Hanson, LLP

(57) ABSTRACT

The present invention provides a nursing care recipient watching support system. In the nursing care recipient watching support system, position information with respect to a measuring position, and indoor compartment attribute information such as a living room, a share room, a conversation room, a kitchen, a bathroom and an entrance, as well as watching level information corresponding to the indoor compartment attribute information are stored in storing unit 30. Position information extracting means 40 extracts the position information, the indoor compartment attribute information and the watching level information. Output means 60 outputs the position information, the indoor compartment attribute information and the watching level information, According to this, it is possible to estimate an
(Continued)

existent position of a nursing care recipient, and to support a watching operation of the nursing care recipient.

12 Claims, 12 Drawing Sheets

(52) U.S. Cl.
CPC ............ *A61B 5/1113* (2013.01); *A61B 5/742* (2013.01); *A61B 5/746* (2013.01)

(58) Field of Classification Search
CPC ........ G08B 25/04; G08B 25/00; G08B 21/02; G01S 5/02
USPC ............ 340/540, 573.1, 573.4, 686.1, 686.6, 340/286.07
See application file for complete search history.

(56) References Cited

U.S. PATENT DOCUMENTS

| | | | | |
|---|---|---|---|---|
| 2014/0379255 | A1* | 12/2014 | Johnson | A61B 5/7405 701/470 |
| 2016/0379476 | A1* | 12/2016 | Sella | A61B 5/1113 340/539.19 |
| 2017/0150905 | A1* | 6/2017 | Shen | A61B 5/11 |

FOREIGN PATENT DOCUMENTS

| | | |
|---|---|---|
| JP | 2005-215961 A | 8/2005 |
| JP | 2007-150435 A | 6/2007 |
| JP | 2011-163948 A | 8/2011 |
| JP | 2013-238964 A | 11/2013 |
| JP | 2018-056713 A | 4/2018 |

* cited by examiner

[Fig. 1]
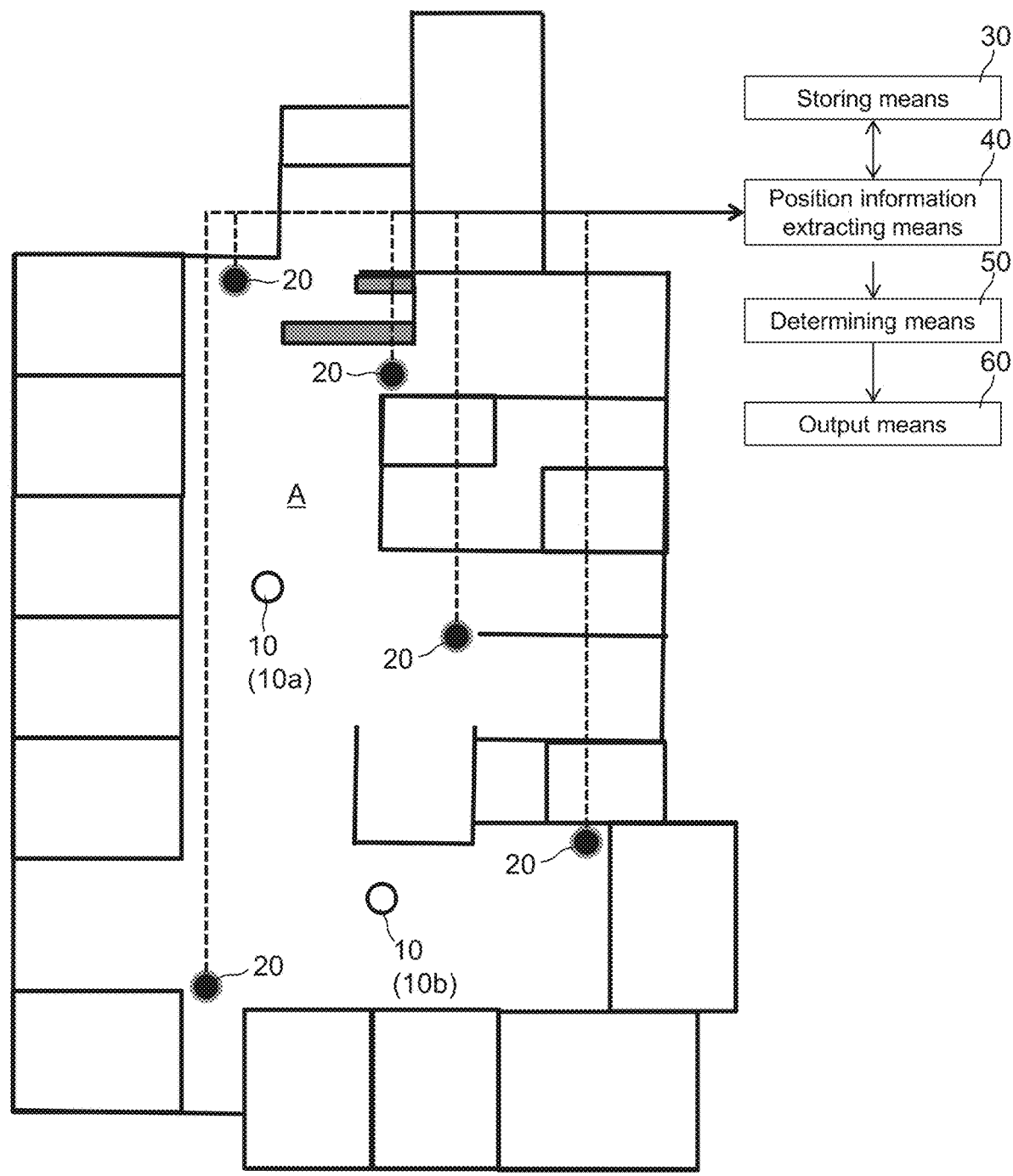

[Fig.2]
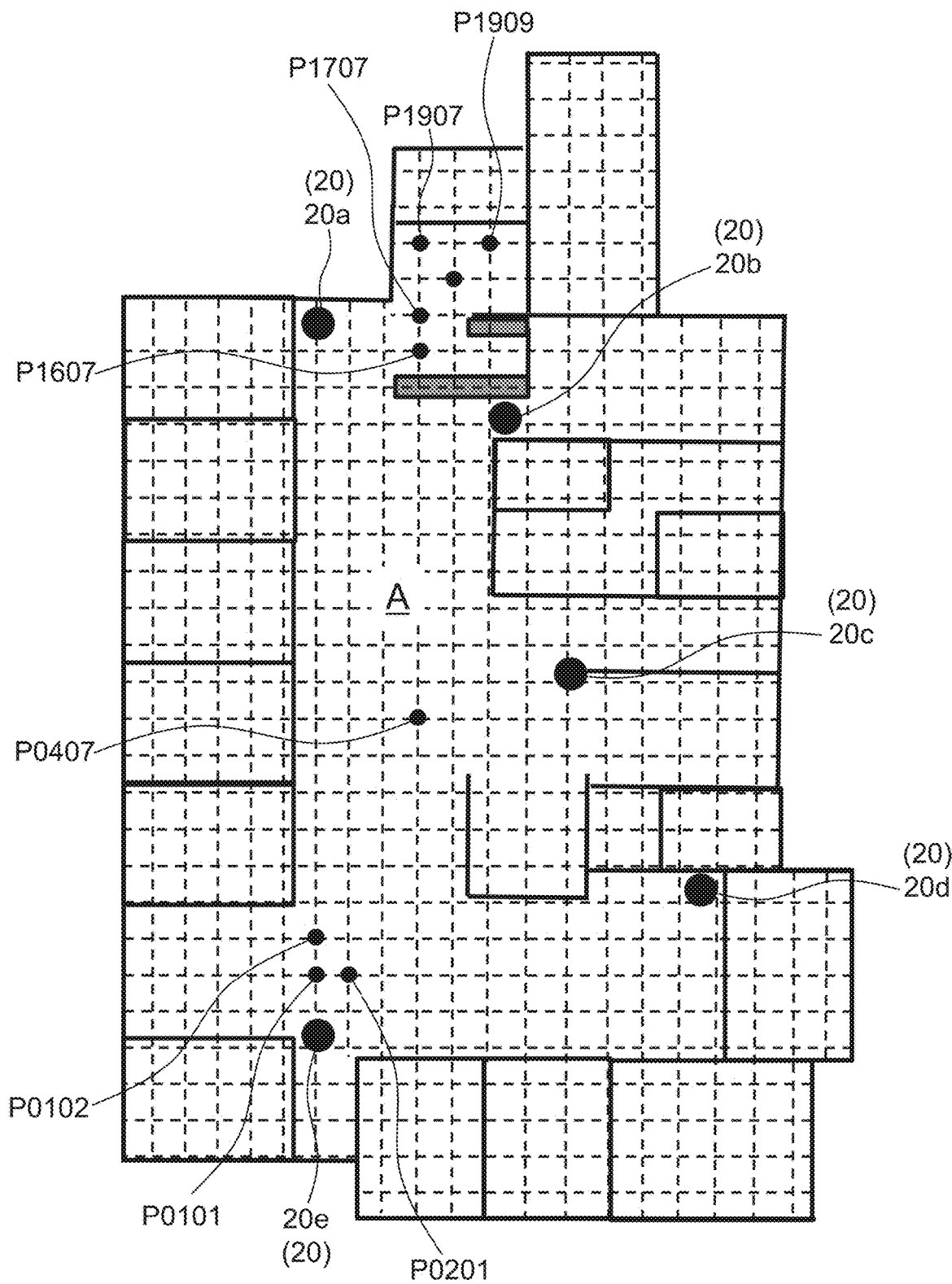

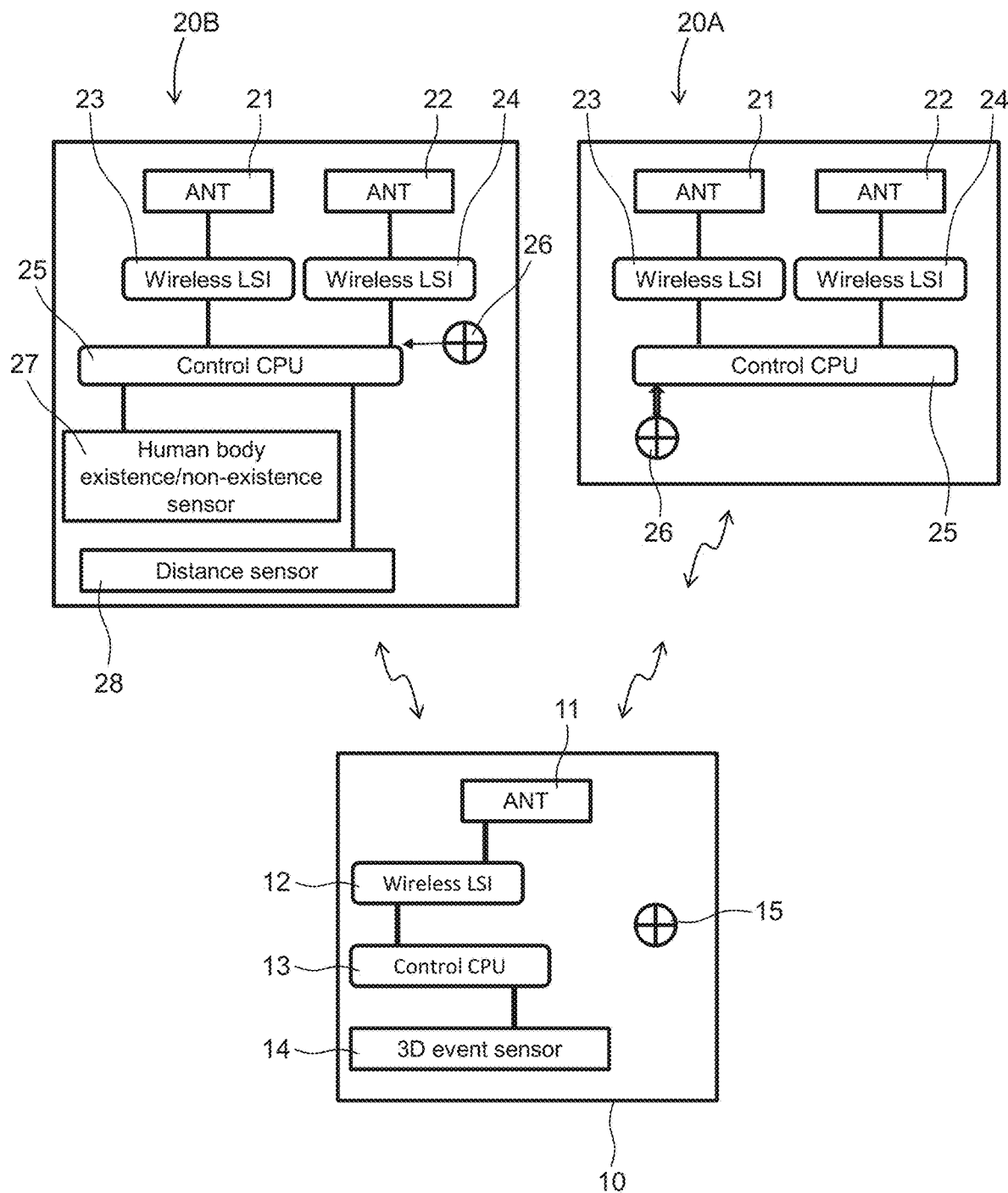

[Fig.4]
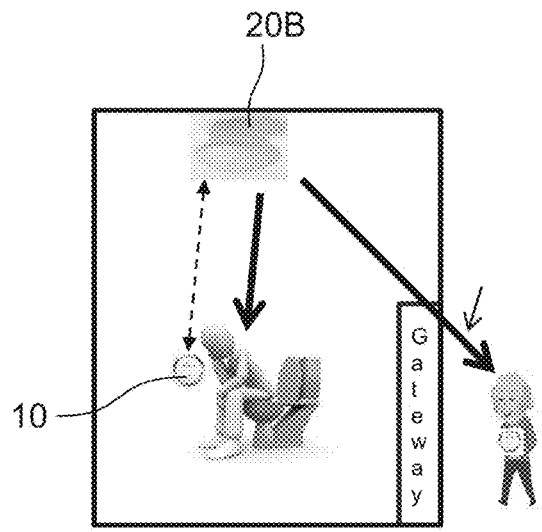
(a)
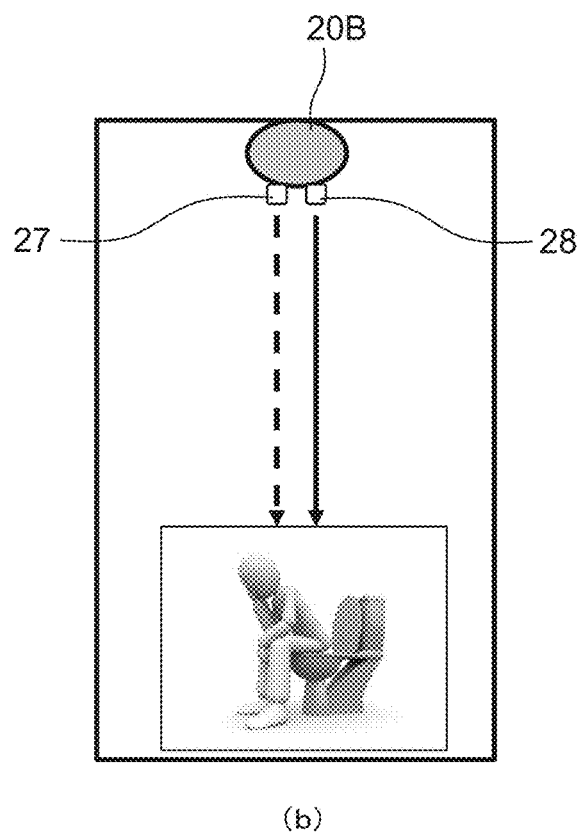
(b)
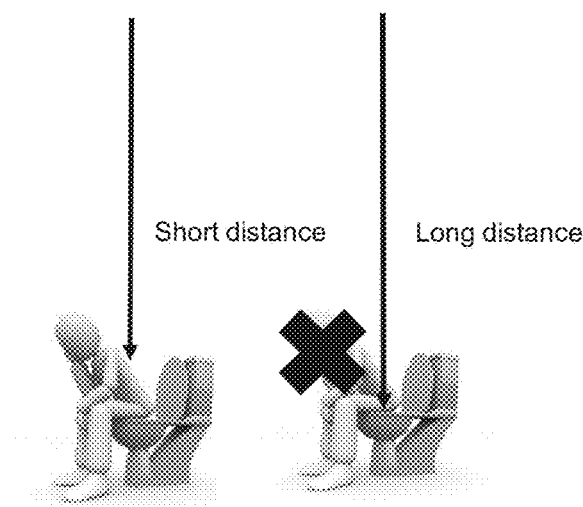
(c)

[Fig.5]
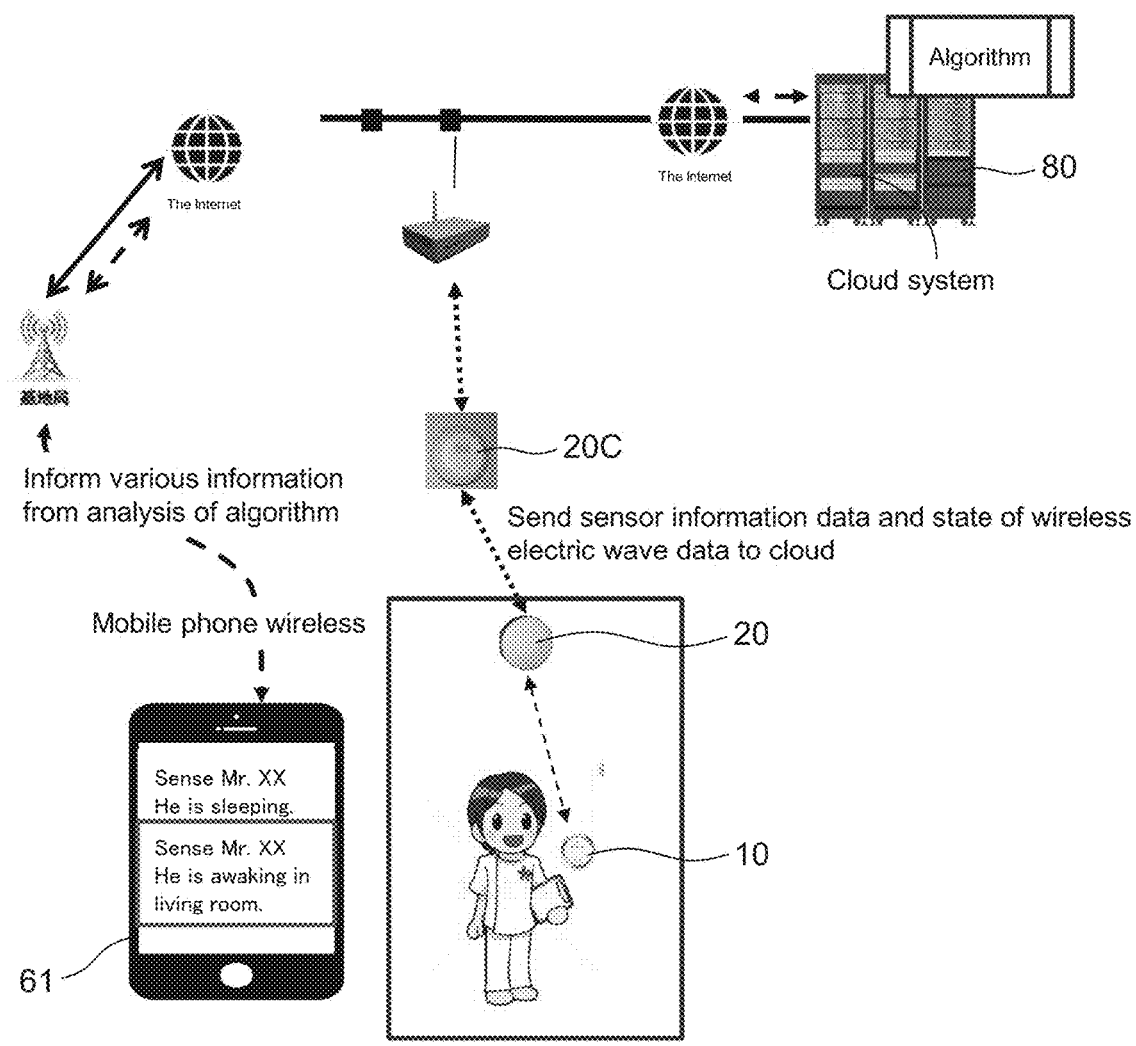

[Fig.6]
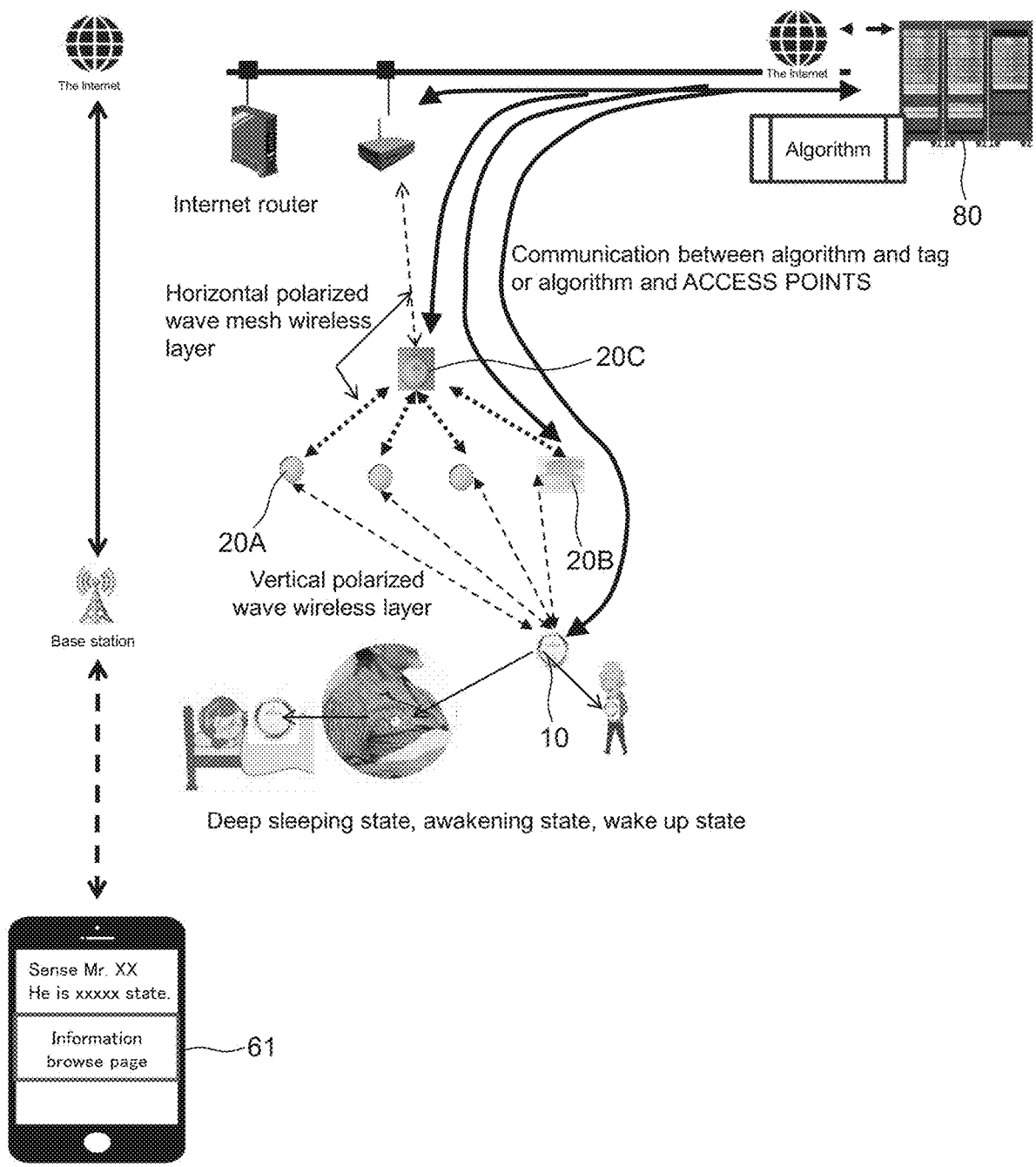

[Fig.7]
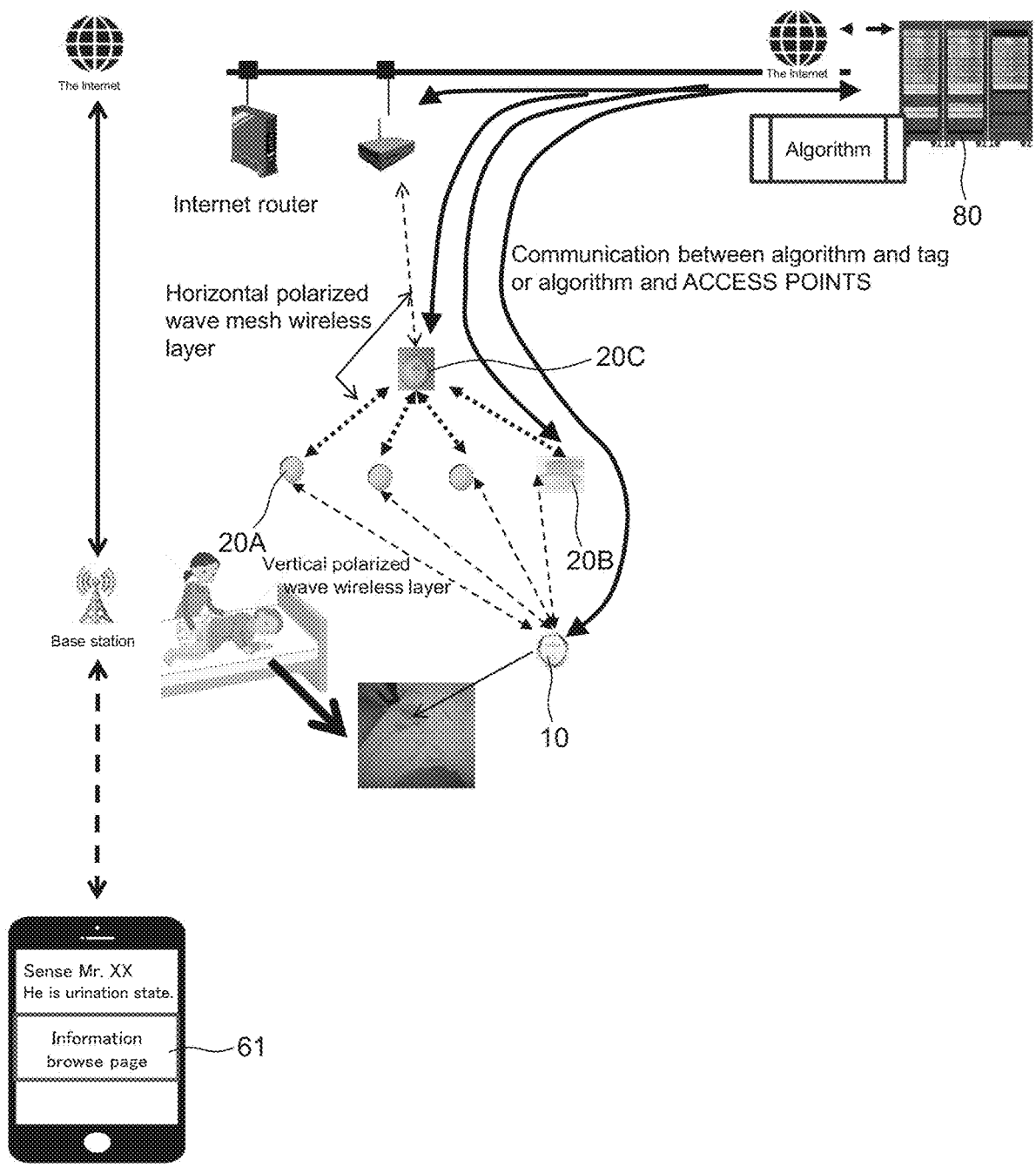

[Fig.8]
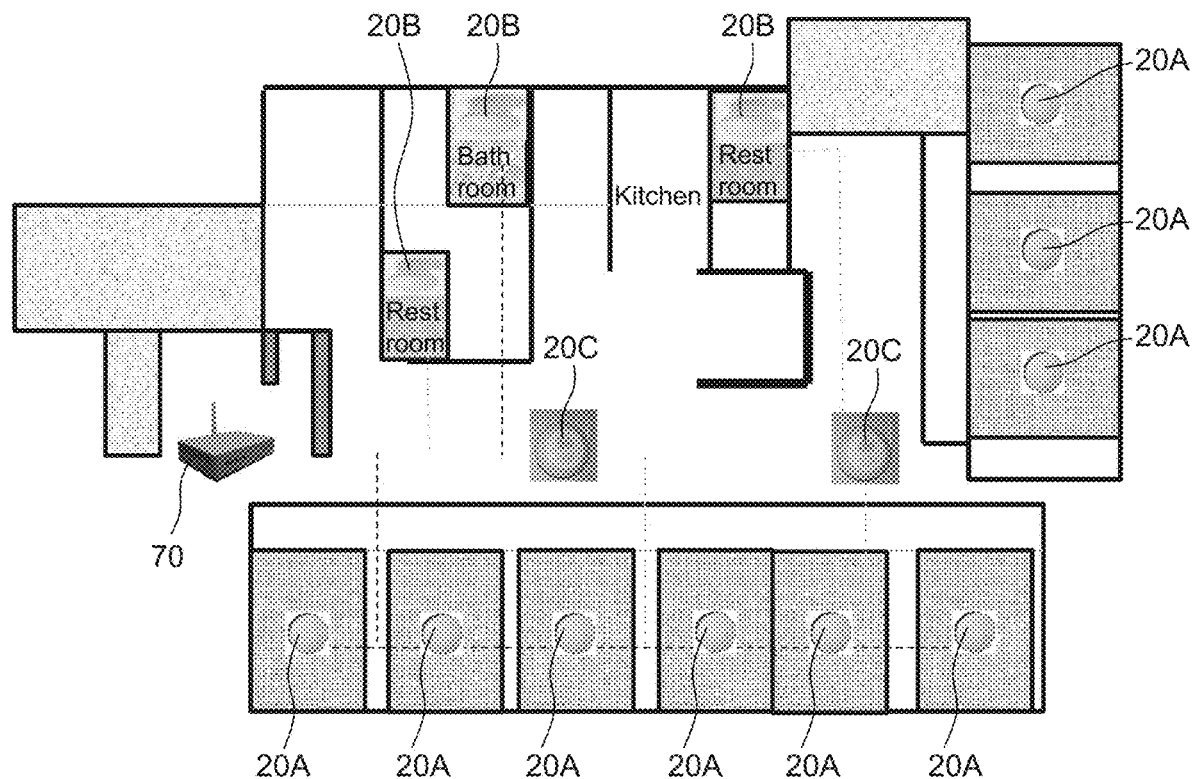
(a)
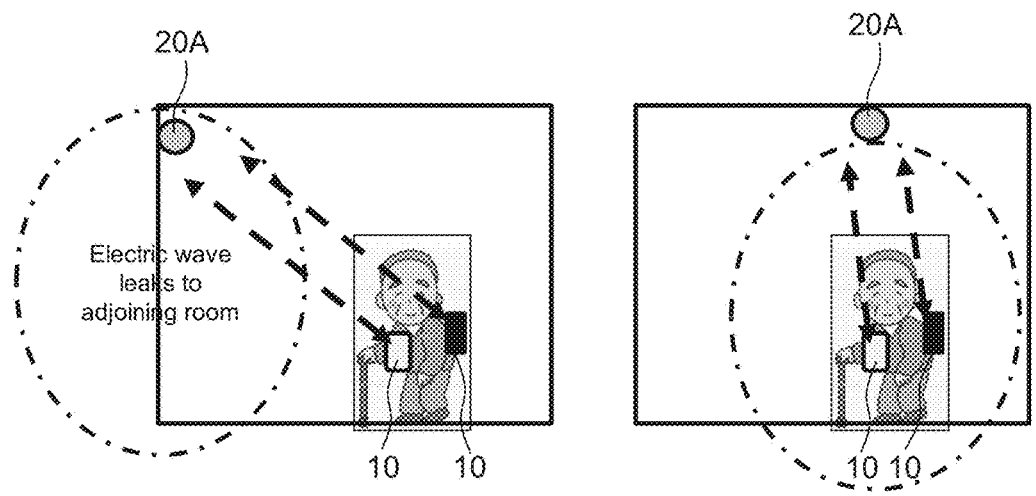
(b)          (c)

[Fig.9]
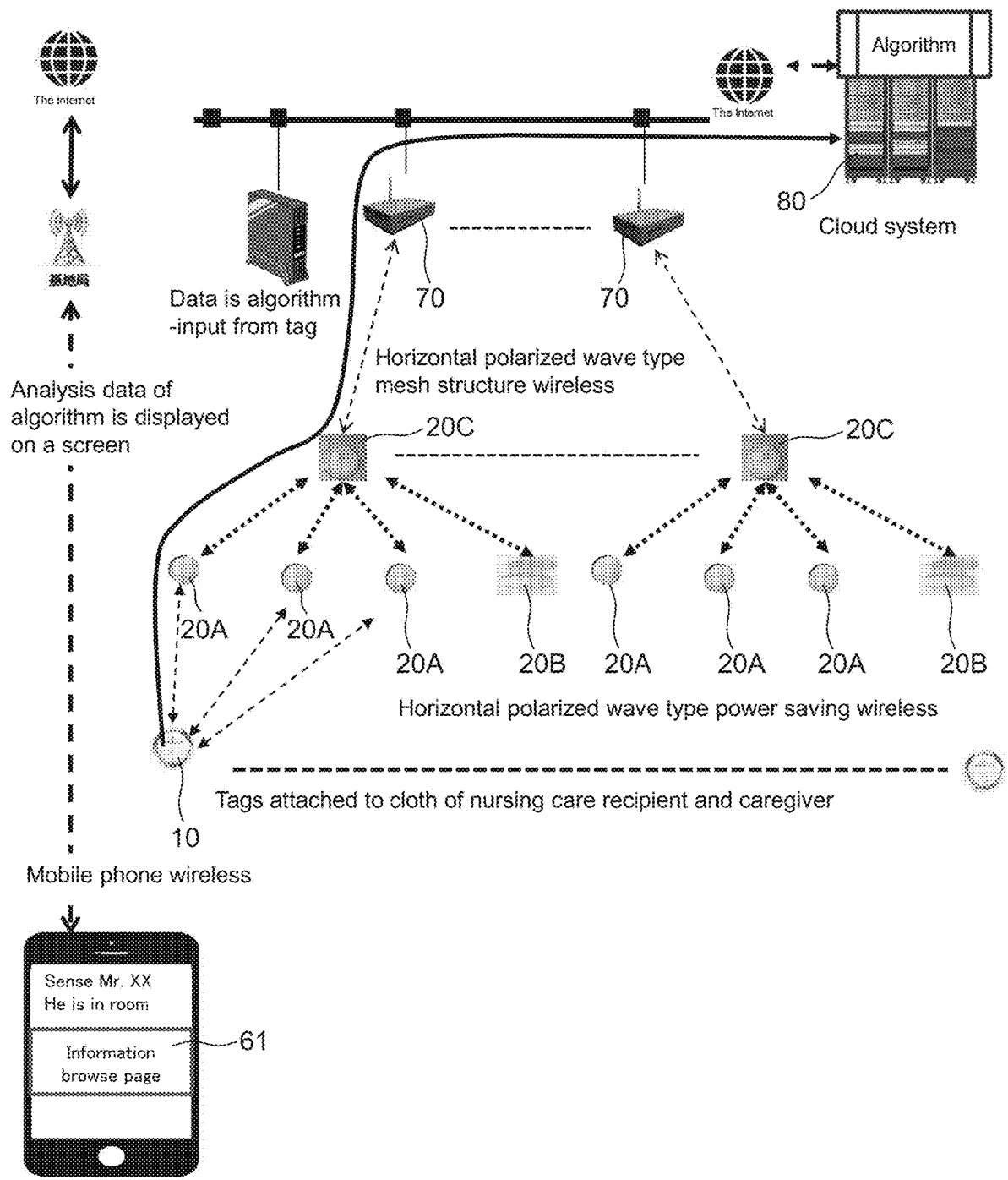

[Fig. 10]
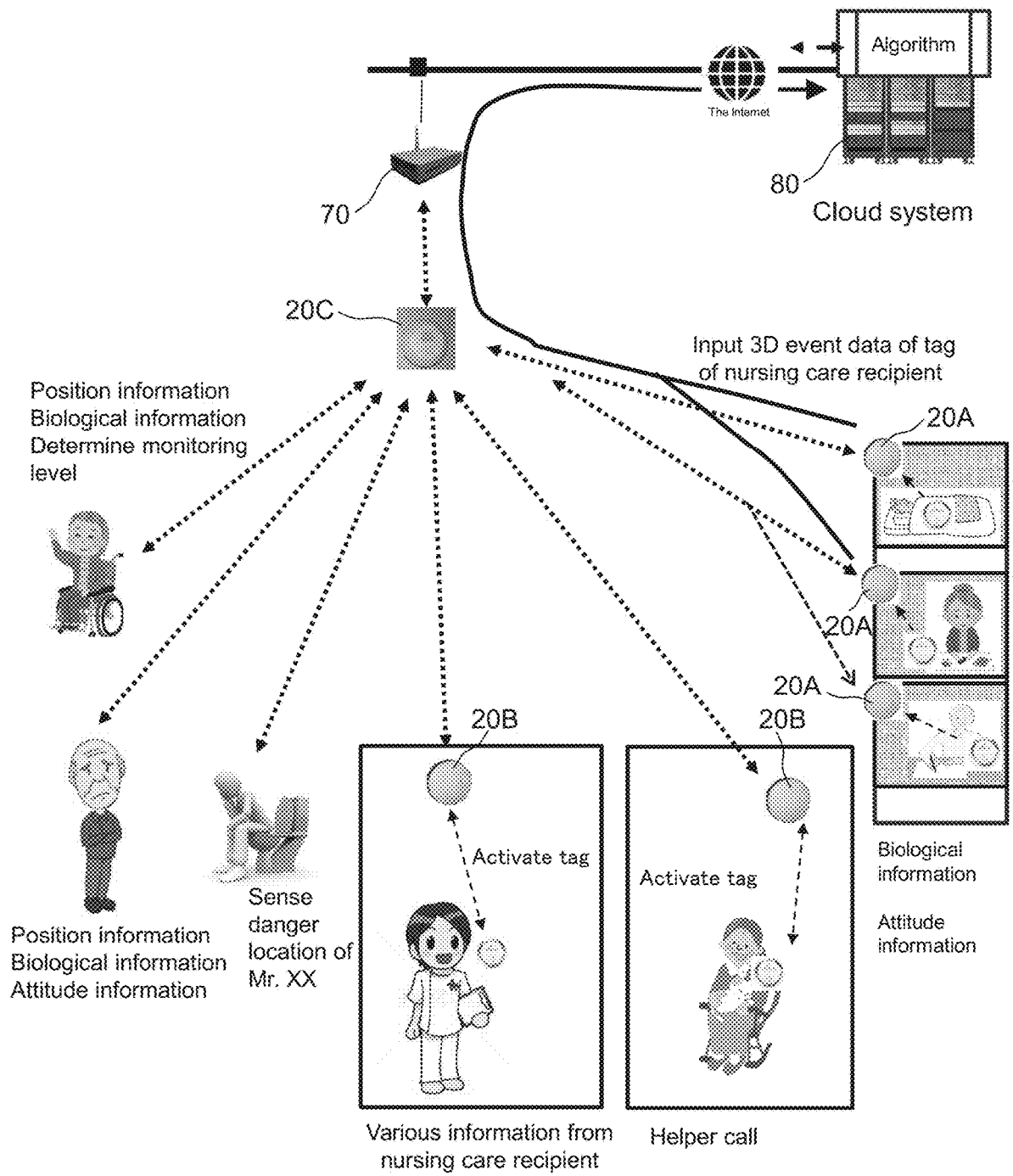

[Fig.11]
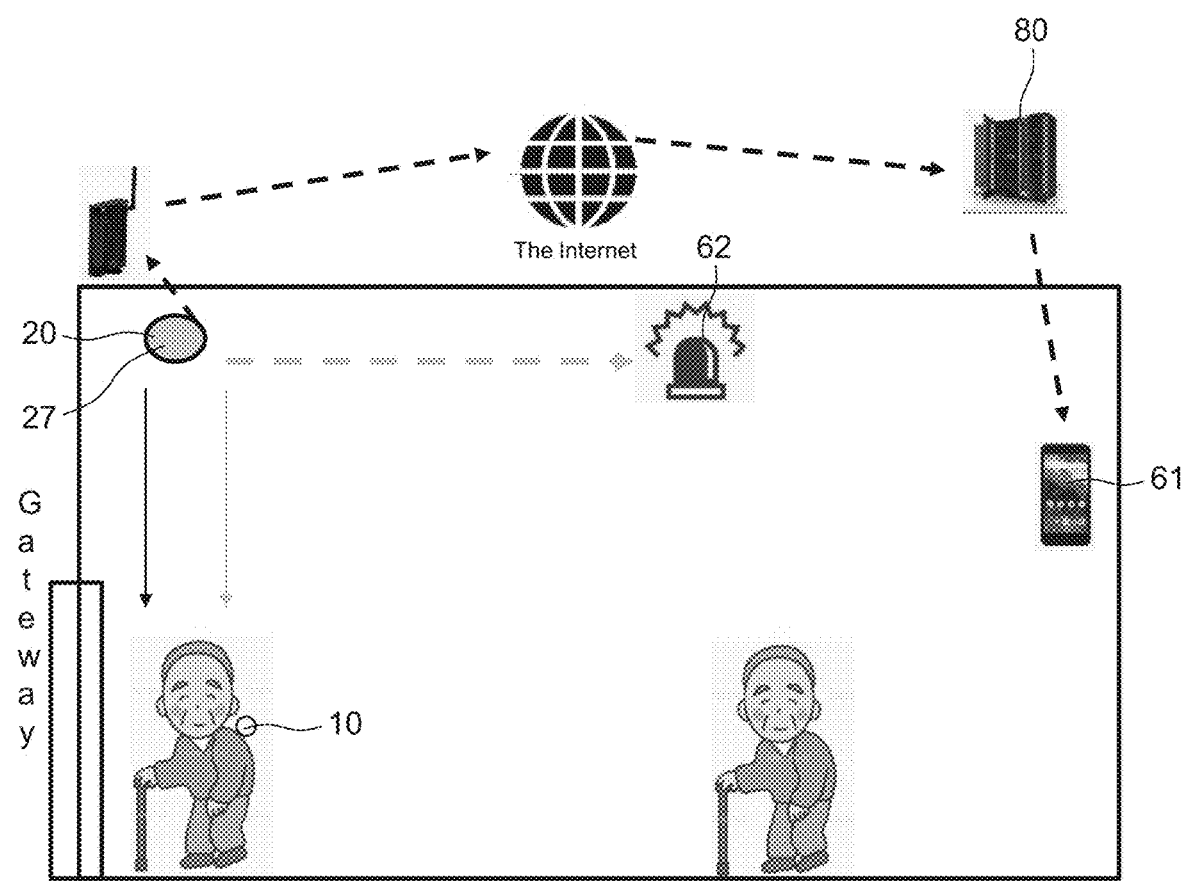

[Fig.12]
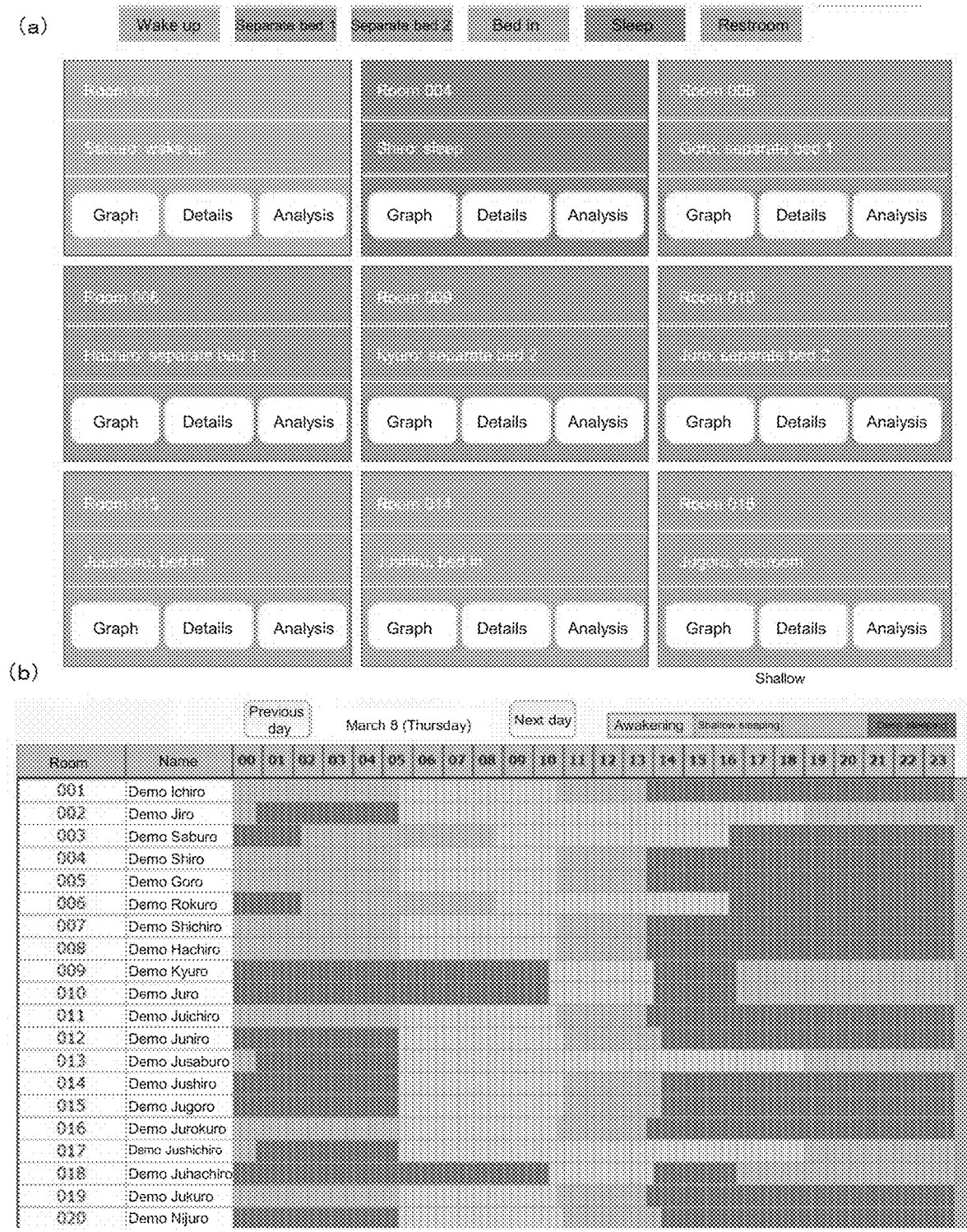

NURSING CARE RECIPIENT WATCHING SUPPORT SYSTEM

TECHNICAL FIELD

The present invention relates to a nursing care recipient watching support system especially used in a geriatric facility.

BACKGROUND TECHNIQUE

In many geriatric facilities, one or two caregivers take care of five to ten elderly people who need nursing care (nursing care recipients), and it is not possible to sufficiently watch them.

Therefore, some facilities regulate free to act of nursing care recipients.

It is possible to watch nursing care recipients utilizing GPS outdoor, but it is difficult to utilize the GPS indoor.

Patent document 1 proposes a communication system capable of immediately and precisely detect a position and a state of an individual person who brings a wireless terminal in a facility where an obstacle such as walls, floors, fixtures and fittings exist.

Patent document 1 includes wireless tags attached to nursing care recipients, a plurality of access points placed at predetermined indoor locations, storing means which stores received signal level from the respective wireless tags at the access points as position estimating signal level pattern together with position information, and position information extracting means which handles a received signal level from the wireless tag at the access point as a detection signal level pattern, which selects one of the position estimating signal level patterns which is closest to the detection signal level pattern, and which extracts position information of the selected position estimating signal level pattern. According to this, it is possible to estimate an existent position of a nursing care recipient in a room from the position information extracted by the position information extracting means.

Patent document 1 suggests informing means for informing when a nursing care recipient is located at a specific region, when the nursing care recipient moves to outside of the specific region, or when moving speed is out of specific range.

PRIOR ART DOCUMENT

Patent Document

[Patent Document 1]
Japanese Patent Application Laid-open No. 2007-150435

SUMMARY OF THE INVENTION

Problem to be Solved by the Invention

However, in order to support the watching of a nursing care recipient by a caregiver, it is necessary to grasp rooms where the nursing care recipient exits such as a living room, a share room, a conversation room, a kitchen, a bathroom and an entrance, and to grasp watching level information corresponding to these rooms to handle in accordance with an urgent degree.

Hence, it is an object of the present invention to provide a nursing care recipient watching support system capable of grasping rooms where the nursing care recipient exits such as a living room, a share room, a conversation room, a kitchen, a bathroom and an entrance, and grasping watching level information corresponding to these rooms.

Means for Solving the Problem

Claim 1 of the present invention provides a nursing care recipient watching support system comprising: wireless tags 10 attached to nursing care recipients; a plurality of access points 20 located at predetermined indoor locations; storing means in which the access points 20 are located at the predetermined locations, received signal levels of the wireless tags 10 at the access points 20 are previously measured at a plurality of arbitrary measuring position Ps, and the measured received signal levels are stored in the storing means as position estimating signal level patterns together with position information of the measuring position Ps; and position information extracting means 40 which detects the received signal levels at the access points 20 from the wireless tags 10, which handles the detected received signal levels as detection signal level patterns, which selects the position estimating signal level pattern which is the closest to the detection signal level pattern, and which extracts the position information of the selected position estimating signal level pattern; in which an existent position of the indoor nursing care recipient is estimated from the position information extracted by the position information extracting means 40, and watching of the nursing care recipient is supported, wherein the position information, indoor compartment attribute information such as a living room, a share room, a conversation room, a kitchen, a bathroom and an entrance with respect to the measuring position P, and watching level information corresponding to the indoor compartment attribute information are stored in the storing means, the position information extracting means 40 extracts the position information, the indoor compartment attribute information and the watching level information, and output means 60 outputs the position information, the indoor compartment attribute information and the watching level information.

According to the invention described in claim 2, the nursing care recipient watching support system of claim 1 further includes determining means 50 which estimates a moving direction of the nursing care recipient from the time series position information during continuation of extraction of the same indoor compartment attribute information, which and determines a watching level from the estimated moving direction, wherein when the determining means 50 determines the watching level which is different from the watching level information, the output means 60 outputs the watching level instead of the watching level information.

According to the invention described in claim 3, in the nursing care recipient watching support system of claim 1, the wireless tag 10 includes sending interval changing means for changing sending interval of a sending signal, and the wireless tag 10 changes the sending interval in accordance with the indoor compartment attribute information extracted by the position information extracting means 40, and sends the sending signal.

According to the invention described in claim 4, in the nursing care recipient watching support system of claim 1, watching level changing information corresponding to time zone is stored in the storing means 30, and the output means 60 outputs the watching level information which is changed by the watching level changing information.

According to the invention described in claim 5, in the nursing care recipient watching support system of claim 1, the wireless tag 10 includes a 3D sensor, and the wireless tag 10 outputs a detection value by the 3D sensor as a sending signal.

According to the invention described in claim 6, in the nursing care recipient watching support system of claim 1, a unique identification code is given to the wireless tag 10, nursing care recipient identification information corresponding to the unique identification code and individual watching level information which is set corresponding to the nursing care recipient identification information are stored in the storing means 30, and if the individual watching level information is a watching non-required level or a watching low level, the output means 60 outputs the watching non-required level or the watching low level even if the watching level information is a watching-required level or a watching high level.

According to the invention described in claim 7, in the nursing care recipient watching support system of claim 1, the wireless tag 10 includes a caregiver wireless tag 10b attached to a caregiver who gives care to the nursing care recipient, the position information extracting means 40 extracts the position information of the nursing care recipient and position information of the caregiver, the nursing care recipient watching support system further includes determining means 50 for determining a watching level from the position information of the nursing care recipient and the position information of the caregiver extracted by the position information extracting means 40 when the caregiver does not exists in a predetermined range of the nursing care recipient, and the output means 60 outputs a determination result and the position information when the determining means 50 determines a watching-required level.

According to the invention described in claim 8, in the nursing care recipient watching support system of claim 1, the access point 20 includes a human body existence/non-existence sensor 27 and a distance sensor 28, and an human body existence/non-existence information which is sensed by the human body existence/non-existence, sensor 27 and distance information which is measured by the distance sensor 28 are sent from the access point 20.

According to the invention described in claim 9, in the nursing care recipient watching support system of claim 8, the access point 20 including the human body existence/non-existence sensor 27 and the distance sensor 28 is placed in a restroom, motion to the restroom is estimated by position estimation made by the wireless tag 10, the human body existence/non-existence sensor 27 senses timing of movement into and out from the restroom, and the distance sensor 28 senses a motionlessness state in the restroom.

According to the invention described in claim 10, in the nursing care recipient watching support system of claim 5, the 3D sensor includes a triaxial acceleration sensor, and the triaxial acceleration sensor determines an awaking state, bed-in state, a shallow sleeping state and a deep sleeping state under a condition that the nursing care recipient is located in the living room of the nursing care recipient.

According to the invention described in claim 11, in the nursing care recipient watching support system of claim 1, in the living room where the nursing care recipient sleeps, the access point 20 is placed at a central position of a ceiling surface of the living room, and a flat plate directionality antenna is used as a wireless tag receiving antenna used for the access point 20 located on the ceiling surface of the living room.

According to the invention described in claim 12, in the nursing care recipient watching support system of claim 1, the access point 20 includes a human body existence/non-existence sensor 27, human body existence/non-existence information sensed by the human body existence/non-existence sensor 27 is sent from the access point 20 to a cloud system 80, and the human body existence/non-existence information is sent to a warning output display warning lamp terminal 62 separately from the cloud system 80.

Effect of the Invention

According to the nursing care recipient watching support system of the present invention, it is possible to estimate an existent position of a nursing care recipient existing indoor.

BRIEF DESCRIPTION OF DRAWINGS

FIG. 1 is a block diagram showing a nursing care recipient watching support system of an embodiment of the present invention as function realizing means;

FIG. 2 is an explanatory diagram of a position estimating signal level pattern in the nursing care recipient watching support system;

FIG. 3 is a block diagram showing wireless tags and access points in the nursing care recipient watching support system;

FIG. 4 are conceptual diagrams showing communication between the wireless tags and the access points in the nursing care recipient watching support system;

FIG. 5 is a conceptual diagram showing communication with a care giver in the nursing care recipient watching support system;

FIG. 6 is a concrete conceptual diagram for realizing the nursing care recipient watching support system by a cloud system;

FIG. 7 is another concrete conceptual diagram for realizing the nursing care recipient watching support system by the cloud system;

FIG. 8 are conceptual diagrams showing installation examples of the access points in the nursing care recipient watching support system;

FIG. 9 is a cloud connection diagram with a wireless communication environment in a facility in the nursing care recipient watching support system;

FIG. 10 is a conceptual diagram showing understanding of a whereabouts of a nursing care recipient and its attribute information in the nursing care recipient watching support system;

FIG. 11 is a conceptual diagram of a nursing care recipient watching support system of another embodiment; and FIG. 12 are output screen image diagrams of the nursing care recipient watching support system of the present invention.

MODE FOR CARRYING OUT THE INVENTION

A first embodiment of the present invention provides a nursing care recipient watching support system wherein the position information, indoor compartment attribute information such as a living room, a share room, a conversation room, a kitchen, a bathroom and an entrance with respect to the measuring position, and watching level information corresponding to the indoor compartment attribute information are stored in the storing means, the position information extracting means extracts the position information, the indoor compartment attribute information and the watching level information, and output means outputs the position information, the indoor compartment attribute information and the watching level information. According to this embodiment, it is possible to grasp a room where a nursing care recipient exists such as a living room, a share room, a conversation room, a kitchen, a bathroom and an entrance, and a caregiver can handle the nursing care recipient in accordance with an urgent degree by outputting warning information corresponding to these room.

According to a second embodiment of the invention, the nursing care recipient, watching support system of the first embodiment further includes determining means which estimates a moving direction of the nursing care recipient from the time series position information during continuation of extraction of the same indoor compartment attribute information, and determines a watching level from the estimated moving direction, wherein when the determining means determines the watching level which is different from the watching level information, the output means outputs the watching level instead of the watching level information. According to this embodiment, it is possible to narrow down watching targets to be watched by determining whether the nursing care recipient approaches or separates from a position where the watching level is high.

According to a third embodiment of the invention, in the nursing care recipient watching support system of the first embodiment, the wireless tag includes sending interval changing means for changing sending interval of a sending signal, and the wireless tag changes the sending interval in accordance with the indoor compartment attribute information extracted by the position information extracting means, and sends the sending signal. According to this embodiment, the sending interval can be made long at a position where the watching level is low, and the sending interval can be made shortly when the position has a high watching level. Therefore, life of the battery of the wireless tag can be elongated.

According to a fourth embodiment of the invention, in the nursing care recipient watching support system of the first embodiment, watching level changing information corresponding to time zone is stored in the storing means, and the output means outputs the watching level information which is changed by the watching level changing information. According to this embodiment, it is possible to strengthen the watching operation in a time zone when watch is required, and it is possible to reduce a burden of a caregiver by weakening the watching operation in a time zone where watching is not required.

According to a fifth embodiment of the invention, in the nursing care recipient watching support system of the first embodiment, the wireless tag includes a 3D sensor, and the wireless tag outputs a detection value by the 3D sensor as a sending signal. According to this embodiment, it is possible to watch attitude of a nursing care recipient, and it is possible to estimate a status of a nursing care recipient such as motionlessness, walking, over-turning and sleeping.

According to a sixth embodiment of the invention, in the nursing care recipient watching support system of the first embodiment, a unique identification code is given to the wireless tag, nursing care recipient identification information corresponding to the unique identification code and individual watching level information which is set corresponding to the nursing care recipient identification information are stored in the storing means, and if the individual watching level information is a watching non-required level or a watching low level, the output means outputs the watching non-required level or the watching low level even if the watching level information is a watching-required level or a watching high level. According to this embodiment, it is possible to individually determine nursing care recipients, and it is possible to reduce a burden of a caregiver by narrowing down watching targets to be watched.

According to a seventh embodiment of the invention, in the nursing care recipient watching support system of the first embodiment, the wireless tag includes a caregiver wireless tag attached to a caregiver who gives care to the nursing care recipient, the position information extracting means extracts the position information of the nursing care recipient and position information of the caregiver, the nursing care recipient watching support system further includes determining means for determining a watching level from the position information of the nursing care recipient and the position information of the caregiver extracted by the position information extracting means when the caregiver does not exists in a predetermined range of the nursing care recipient, and the output means outputs a determination result and the position information when the determining means determines a watching-required level. According to this embodiment, since a case where a caregiver exists near the nursing care recipient can be removed from watching targets, it is possible to narrow down targets who are required to be watched.

According to an eighth embodiment of the invention, in the nursing care recipient watching support system of the first embodiment, the access point includes a human body existence/non-existence sensor and a distance sensor, and an human body existence/non-existence information which is sensed by the human body existence/non-existence sensor and distance information which is measured by the distance sensor are sent from the access point. According to this embodiment, it is possible to more reliably watch in a specific area such as a gateway like a restroom and a front door.

According to a ninth embodiment of the invention, in the nursing care recipient watching support system of the eighth embodiment, the access point including the human body existence/non-existence sensor and the distance sensor is placed in a restroom, motion to the restroom is estimated by position estimation made by the wireless tag, the human body existence/non-existence sensor senses timing of movement into and out from the restroom, and the distance sensor senses a motionlessness state in the restroom. According to this embodiment, it is possible to enhance the watching function in a restroom where a watching level is high.

According to a tenth embodiment of the invention, in the nursing care recipient watching support system of the fifth embodiment, the 3D sensor includes a triaxial acceleration sensor, and the triaxial acceleration sensor determines an awaking state, bed-in state, a shallow sleeping state and a deep sleeping state under a condition that the nursing care recipient is located in the living room of the nursing care recipient. According to this embodiment, the present invention can be utilized also for watching at day-and-night time by watching night time behavior history and a sleeping state of a nursing care recipient.

According to an eleventh second embodiment of the invention, in the nursing care recipient watching support system of the first embodiment, in the living room where the nursing care recipient sleeps, the access point is placed at a central position of a ceiling surface of the living room, and a flat plate directionality antenna is used as a wireless tag receiving antenna used for the access point located on the ceiling surface of the living room. According to this embodiment, it is possible to reduce a construction structural problem in a facility and influence cause by an attaching position of the wireless tag.

According to a twelfth of the invention, in the nursing care recipient watching support system of the first embodiment, the access point includes a human body existence/non-existence sensor, human body existence/non-existence information sensed by the human body existence/non-existence sensor is sent from the access point to a cloud system, and the human body existence/non-existence information is sent to a warning output display warning lamp terminal separately from the cloud system. According to this embodiment, it is possible to prevent the output from being delayed, and to inform more quickly.

EMBODIMENTS

A nursing care recipient watching support system according to one of embodiments of the present invention will be described below.

FIG. 1 is a block diagram showing the nursing care recipient watching support system of the embodiment by means of function realizing means.

The nursing care recipient watching support system of the embodiment includes wireless tags 10 attached to nursing care recipients, a plurality of access points 20 placed at predetermined locations in doors A, storing means 30, position information extracting means 40, determining means 50, and output means 60. The nursing care recipient watching support system estimate an existent position of the nursing care recipient in doors A.

Unique identification codes are allocated to the wireless tags 10. The nursing care recipients can be identified by the unique identification codes. It is possible to identify whether a person is a nursing care recipient or a caregiver by the unique identification code. Unique identification information is sent, from the wireless tag 10 as one of sending data. The wireless tags 10 include a wireless tag 10a attached to the nursing care recipient, and a caregiver wireless tag 10b attached to the caregiver who gives care to the nursing care recipient.

The wireless tag 10 includes sending interval changing means for changing sending interval of a sending signal, and it is possible to change the sending interval in accordance with indoor compartment attribute information extracted by the position information extracting means 40, and to send the sending signal. The wireless tag 10 receives the indoor compartment attribute information extracted by the position information extracting means 40 from the access point 20 or another sending means. By changing the sending interval in accordance with the indoor compartment attribute information and sending the sending signal, it is possible to elongate the sending interval at a position where the watching level is low, and to shorten the sending interval only at the position having the high watching level. Therefore, a battery life of the wireless tag 10 can be increased.

The wireless tag 10 includes a 3D sensor, and a detection value of the 3D sensor is output from the wireless tag 10 as a sending signal. The detection value of the 3D sensor is output as the sending signal. According to this, it is possible to watch attitude of a nursing care recipient, and to estimate a situation of the nursing care recipient such as motionlessness, walking, over-turning and sleeping.

The storing means 30 stores the position estimating signal level pattern together with measured position information. The position estimating signal level pattern is a received signal level obtained by previously measuring received signal levels from the wireless tags 10 at access point 20 at a plurality of arbitrary measuring positions at the respective measured access point 20 after the access point 20 are placed at predetermined locations.

Indoor compartment attribute information such as a living room, a share room, a conversation room, a kitchen, a bathroom and an entrance with respect to the measuring position is stored in the storing means 30.

Further, watching level information corresponding to the indoor compartment attribute information is stored in the storing means 30. For example, watching need of a passageway in front of the living room is low and therefore, a watching level of the passageway is 1. There is a possibility that the nursing care recipient enters the bathroom when the nursing care recipient exists around the bathroom, and therefore, it is necessary to watch therein and therefore, the watching level thereof is 2. There is a possibility that a passageway in front of a front door comes out from the front door and the watching need is high and therefore, the watching level of the passageway in front of the front door is 3. A watching level of a restroom is 4. Here, the watching level 4 is higher than the watching level 3, the watching level 3 is higher than the watching level 2, and the watching level 2 is higher than the watching level 1.

Nursing care recipient identification information and caregiver identification information corresponding to the unique identification code, and individual watching level information which is set to correspond to the nursing care recipient identification information are stored in the storing means 30. For example, the individual watching level information is set such that when watching need of a nursing care recipient is zero, the watching level information of that nursing care recipient is "there is no need of watching", when watching need of a nursing care recipient is low, the watching level information of that nursing care recipient is "watching level is low", when it is necessary to watch a nursing care recipient, the watching level information of that nursing care recipient is "it is necessary to watch", and when the need of watching of a nursing care recipient is high, the watching level information of that nursing care recipient is "the watching level is high".

Watching level changing information corresponding to time zone is stored in the storing means 30. Here, this time zone includes time zone exceeding 24 hours like weekdays and non-working days in addition to time zone within 24 hours such as time zone from 8 to 20 hours and time zone from 20 to 8 hours. That is, the watching level changing information corresponding to time zone is information for changing watching level to low watching level or to no need watching level if time zone is daytime time zone when the watching is not so required even if the watching level information indicates high watching level, and for changing watching level to high watching level or need of watching if time zone is nighttime time zone when watching is required even if the watching level information indicates low watching level. It is also possible that the determining means 50 determines using the watching level changing information to change the watching level.

The position information extracting means 40 detects received signal levels at the respective access points 20 from the wireless tags 10, handles the respective received signal levels as detection signal level patterns, selects a position estimating signal level pattern which is closest to the detection signal level pattern, and extracts, from the storing means 30, position information of the selected position estimating signal level pattern together with unique identification code.

The position information extracting means 40 extracts the indoor compartment attribute information and the watching level information together with the position information.

When nursing care recipient identification information and caregiver identification information corresponding to the unique identification code are stored in the storing means 30, the position information extracting means 40 extracts the nursing care recipient identification information and the caregiver identification information.

The determining means 50 determines a watching level in chronological order from the position information extracted by the position information extracting means 40 and from the indoor compartment attribute information. That is, the determining means 50 estimates a moving direction of a nursing care recipient from the time series position information during continuation of extraction of the same indoor compartment attribute information, and determines the watching level from the estimated moving direction.

When a caregiver does not exist in a predetermined range of a nursing care recipient from position information of a nursing care recipient extracted by the position information extracting means 40 and from position information of the caregiver, the determining means 50 determines a watching-required level. Instead of the position information, it is also possible to use the indoor compartment attribute information for determination. That is, if a caregiver does not exist in the same indoor compartment, the determining means 50 determines a watching-required level or a watching high level even if a nursing care recipient exists in a watching non-required level or a watching low level. Further, if a caregiver exists in the same indoor compartment, the determining means 50 determines the watching non-required level or the watching low level even if a nursing care recipient exists in the indoor compartment of the watching-required level or the watching high level.

The output means 60 outputs indoor compartment attribute information and watching level information together with position information extracted by the position information extracting means 40. The output means 60 outputs nursing care recipient identification information and caregiver identification information. By outputting the nursing care recipient identification information and the caregiver identification information together with the position information, it is possible to separately determine a nursing care recipient and a caregiver.

When watching level information is output on a monitor (display means), watching level information such as dangerousness is displayed by means of characters or a numeric value, or position information sets are displayed by different colors, or position information is displayed in a blinking manner. It is also possible to output watching level information differently by means of sound or warning sound.

By outputting the watching level information together with the position information, it is possible to reliably watch a nursing care recipient who enters a danger region such as a passageway in front of the front door.

When the determining means 50 determines a watching level which is different from watching level information, the output means 60 outputs determined watching level instead of the watching level information.

The output means 60 outputs position information in a predetermined time period in chronological order. By outputting the position information in chronological order, it is possible to affirm a moving path of a nursing care recipient, and to form trace files for every nursing care recipient and caregiver.

When the determining means 50 determines a watching-required level, the output means 60 outputs a determination result together with position information. When the watching level is determined in chronological order using the position information and the indoor compartment attribute information, it is possible to narrow down persons to be watched by estimating a moving direction of a nursing care recipient from the time series position information during continuation of extraction of the same indoor compartment attribute information, and by determining the watching level from the moving direction which is estimated that the nursing care recipient approaches or separates from a position having a high watching level. When a caregiver does not exist within a predetermined range of the nursing care recipient from position information of the nursing care recipient and position information of the caregiver, if the watching level is determined, a case where the caregiver exists near the nursing care recipient can be removed from a person to be watched. Therefore, it is possible to narrow down persons who are required to be watched.

When watching level changing information corresponding to time zone is stored in the storing means 30, the output means 60 outputs watching level information which is changed by the watching level changing information. For example, even if the watching level information is watching high level, if that time is in daytime time zone when it is not so required to watch, a watching level is changed to a watching low level or a watching non-required level, and even if the watching level information is watching low level, if that time is in the nighttime time zone when watch is required, watching level is changed to a watching high level or a watching-required level. Therefore, it is possible to strengthen the watching in time zone when watching is required, and it is possible to reduce a burden on a caregiver by softening the watching in time zone such as holiday when a family exists.

When individual watching level information which is set corresponding to the nursing care recipient identification information is stored in the storing means 30, if individual watching level information is watching non-required level or watching low level, the output means 60 outputs a watching non-required level or a watching low level even if watching level information is a watching-required level or a watching high level, and if the individual watching level information is a watching-required level or a watching high level, the output means 60 outputs a watching-required level or a watching high level even if the watching level information is a watching non-required level or a watching low level. As described above, by setting the individual watching level information corresponding to the nursing care recipient identification information, it is possible to individually determine nursing care recipients, and to reduce a burden of a caregiver by narrowing down persons to be watched. It is also possible to change the watching level if the determining means 50 determines using the individual watching level information.

FIG. 2 is an explanatory diagram of a position estimating signal level pattern in the nursing care recipient watching support system according to the embodiment.

In order to set the position estimating signal level pattern, the access points 20 are previously placed at predetermined locations.

FIG. 2 shows a state where five access points 20*a*, 20*b*, 20*c*, 20*d* and 20*e* are placed.

Next, arbitrary measuring positions are determined for areas indoor A where a nursing care recipient and a caregiver can act. For example, the areas where the nursing care recipient and the caregiver can act are divided into a lattice shape, and lattice points thereof are determined as measuring positions P.

Measuring positions P0101, P0102, P0201, P1607, P1707, P1907 and P1909 shown in FIG. 2 are representative positions for the following description, and all of the lattice points are determined as measuring positions. Although all of the area are partitioned into the lattice shape and all of the lattice points are determined as the measuring positions, areas having a high watching level may be placed densely and areas having a low watching level may be placed sparsely corresponding to the indoor compartment attribute information.

The wireless tags 10 are placed at the lattice points, and received signal levels at the five access points 20a, 20b, 20c, 20d and 20e are measured.

For example, suppose that a received signal level of the access point 20a is 82, a received signal level of the access point 20b is 88, a received signal level of the access point 20c is 52, a received signal level of the access point 20d is 71, and a received signal level of the access point 20e is 90. This case is expressed by "p0101=(82, 88, 52, 71, 90). This P0101=(82, 88, 52, 71, 90) is a position estimating signal level pattern at the measuring position P0101.

Here, suppose that position estimating signal level patterns at the measuring positions P shown in FIG. 2 are as follows.

P0101=(82, 88, 52, 71, 90),

P0102=(85, 88, 52, 71, 90),

P0201=(90, 88, 52, 71, 90),

P1607=(95, 50, 30, 10, 42),

P1707=(98, 52, 33, 15, 40),

P1907=(92, 55, 29, 16, 38),

P1909=(92, 51, 34, 12, 39), and

P0407=(70, 95, 95, 30, 88).

In the case of the indoor A as in the embodiment, electric wave reflects on a wall or a ceiling. Therefore, a received signal level does not have correlation with a simple distance and vision between the wireless tags 10 and the access points 20.

A case where position estimating signal level patterns at the respective measuring positions are stored will be described below concerning an extracting method of position information.

If a detection signal pattern detected from the wireless tags 10 attached to a nursing care recipient is (70, 95, 95, 30, 88), since this coincides with a position estimating signal level pattern at the measuring position P0407, it is possible to estimate that a nursing care recipient exists at the measuring position P0407.

A case where a detection signal pattern detected by a wireless tag 10 attached to a nursing care recipient does not coincide with a position estimating signal level pattern, e.g., a case where a detection signal pattern is (86, 88, 52, 71, 90) will be described.

In this case, although a position estimating signal level pattern which coincides with the detection signal pattern (86, 88, 52, 71, 90) does not exists, there are measuring positions P0101, P0102 and P0201 as position estimating signal level patterns which are close to the detection signal pattern. In this case, since the position estimating signal level pattern which is closest to the detection signal pattern (86, 88, 52, 71, 90) is the measuring position P0102 (85, 88, 52, 71, 90), it is estimated that the nursing care recipient exists at the measuring position P0102.

Next, watching level information will be described.

Concerning measuring positions P0101, P0102, P0201 and P0407, indoor compartment attribute information is the passageway in front of the living room, and the need of watching is low. Therefore, watching level information which is a watching level 1 is previously stored.

Concerning measuring positions P1607, P1707, P1907 and P1909 on the other hand, indoor compartment attribute information is the passageway in front of the front door, and there is a possibility that the nursing care recipient comes out from the front door, and the need of watching is high. Therefore, watching level information which is a watching level 3 is previously stored.

Next, a case where a watching level is determined in chronological order from position information and indoor compartment attribute information will be described.

Concerning measuring positions P1607, P1707, P1907 and P1909, the watching level information is the watching level 3. Therefore, the determining means 50 estimates a moving direction of a nursing care recipient from the time series position information during continuation of extraction of the same indoor compartment attribute information, and determines the watching level from the estimated moving direction.

In this case, if the time series position information is movement from the measuring position P1909 to the measuring position P1907, since a degree of danger that the nursing care recipient comes out from the front door is high, the determining means 50 determines to increase the watching level or determines to continue the watching level 3. If the time series position information is movement from the measuring position P1909 to the measuring position P1607, since the degree of danger that the nursing care recipient comes out from the front door is low, the determining means 50 determines to reduce the watching level, e.g., determines the watching level 2. By estimating the moving direction of the nursing care recipient from the time series position information during continuation of extraction of the same indoor compartment attribute information, and by determining the watching level from the estimated moving direction, it is possible to estimate future action of the nursing care recipient, i.e., the moving direction to change the watching level. According to this, it is possible to narrow down persons to be watched by changing the preset watching level.

FIG. 3 is a block diagram showing wireless tags and access points in the nursing care recipient watching support system of the embodiment.

The wireless tag 10 is a small and light-weighted disk-shaped casing wearable terminal corresponding to 10 yen coin, and the wireless tag 10 is attached to clothes of a nursing care recipient. One of surfaces of the disk-shaped casing includes an electric wave absorbing body membrane. The one surface having the electric wave absorbing body membrane is attached as a human body side surface. According to this, influence of electric wave exerted on a human body is reduced.

The wireless tag 10 includes a disk-shaped electronic substrate, and an antenna 11, a wireless LSI 12, a control CPU 13 and a 3D event sensor 14 are mounted on the electronic substrate, and the wireless tag 10 also includes a battery 15 for driving these members. The antenna 11 is of a chip-type, and has a heart-shaped directionality. The wireless LSI 12 seizes beacon electric wave from high-order or superior network, recognizes the wireless LSI 12 itself, groups data of the 3D event sensor 14 into a packet in specific communication fashion, and sends the packet to a high-order or superior access point every time. If a signal level of the 3D event sensor 14 exceeds a threshold value, the control CPU 13 drives the wireless LSI 12 to establish energy-saving battery driving. The 3D event sensor 14 outputs 3D data, and the data is put onto a high-order or superior cloud system 80 (see FIG. 5) through a first access point 20A and a second access point 20B, a unique identification code of the wireless tag 10 and the 3D data are secured in the cloud system 80 and various determinations are made. A primary battery can be used as the battery 15, and a coin-type lithium battery can be used. The cloud system 80 includes the storing means 30, the position information extracting means 40 and the determining means 50 shown in FIG. 1.

As the access points 20, there are the first access point 20A and the second access point 20B.

The first access point 20A includes an electronic substrate, and a first antenna 21, a second antenna 22, a first wireless LSI 23, a second wireless LSI 24 and a control CPU 25 are mounted on the electronic substrate. The first access point 20A includes a battery 26 for driving these members, and the first access point 20A is placed mainly for the living room.

The second access point 20B includes an electronic substrate, and a first antenna 21, a second antenna 22, a first wireless LSI 23, a second wireless LSI 24, a control CPU 25, a human body existence/non-existence sensor 27 and a distance sensor 28 are mounted on the electronic substrate. The second access point 20B includes a battery 26 for driving these members, and the second access point 20B is placed for a restroom. A pyroelectric-type sensor can be used as the human body existence/non-existence sensor 27, and an ultrasonic sound sensor or a laser sensor can be used as the distance sensor 28. Existence/non-existence information sensed by the human body existence/non-existence sensor 27 and distance information measured by the distance sensor 28 are sent from the access point 20B.

The battery 26 of the first access point 20A and the battery 26 of the second access point 20B are secondary batteries. On a place where an AC source can be connected, the AC source is connected to the first access point 20A and the second access point 20B.

The first antenna 21 is a flat plate directionality antenna (patch antenna), the second antenna 22 is a horizontal polarized wave antenna, the first antenna 21 is connected to the first wireless LSI 23, and the second antenna 22 is connected to the second wireless LSI 24.

The first wireless LSI 23 conducts wireless electric wave communication with the wireless LSI 12 of the wireless tag 10. The second wireless LSI 24 is connected to a wireless router which is connected to the Internet by wireless electric wave communication which is different from communication with the wireless tag 10.

As described above, the access point 20 as one communication means includes the first wireless LSI 23 which conducts communication with the wireless LSI 12 of the wireless tag 10 and the second wireless LSI 24 which conducts the high-order or superior Internet connection. By using the vertical polarized wave type first antenna 21 and the horizontal polarized wave type second antenna 22, it is possible to prevent radio interference of electric wave, to prevent radio interference with wireless electric wave having other usage in the facility, and to enhance communication quality.

The control CPU 25 parallel-controls the first wireless LSI 23 and the second wireless LSI 24 by a command cord in the control CPU 25. The control CPU 25 conducts communication with the wireless LSI 12 of the wireless tag 10 by the first wireless LSI 23, routes a signal received by the first wireless LSI 23, and sends the same from the second wireless LSI 24. The control CPU 25 sends signals from the human body existence/non-existence sensor 27 and the distance sensor 28 from the second wireless LSI 24.

The human body existence/non-existence sensor 27 and the distance sensor 28 are used as human body sensors. The human body existence/non-existence sensor 27 senses moving motion into and out from a specific area, and a signal is output by moving in and out motion of a human with respect to the specific area. The distance sensor 28 senses attitude of a human in a motionless state, and seize infrared ray which is always generated from a human, and a signal is output. For example, a distance from the access point 20B to a nursing care recipient in the attitude when a nursing care recipient sits on a toilet is previously set as a normal distance. When the distance sensor 28 is sensing the normal distance, it is determined that there is no abnormal state, and when the distance sensor 28 does not sense the normal distance, it is determined that there is the abnormal state.

FIG. 4 are conceptual diagrams showing communication between the wireless tags and the access points in the nursing care recipient watching support system of the embodiment.

FIG. 4(a) shows a case where the second access point 20B shown in FIG. 3 is placed in the restroom.

The human body existence/non-existence sensor 27 can sense the timing when a nursing care recipient moves into and out from the specific area such as the restroom, but if the nursing care recipient is in the motionless state in the restroom, the human body existence/non-existence sensor 27 cannot sense this state.

Motion of the nursing care recipient reaching the door of the restroom is estimated by a position estimation made by the wireless tag 10, the human body existence/non-existence sensor 27 senses the timing when the nursing care recipient opens the door and moves into and out from the restroom, and the distance sensor 28 senses a state of the nursing care recipient staying in the restroom. The state of the nursing care recipient in the restroom tracks a degree of danger by an ID value of a nursing care recipient provided in the wireless tag 10 and by logical sum detected by the distance sensor 28. The human body existence/non-existence sensor 27 senses timing when the nursing care recipient goes out from the restroom, and motion of the nursing care recipient thereafter is sensed by position estimation made by the wireless tag 10.

In many facilities, much time is spent for watching maintenance of a private room such as a restroom, and the effect is great for reducing a burden of a caregiver and for saving human life.

As shown in FIG. 4(b), the access point 20B includes the human body existence/non-existence sensor 27 and the distance sensor 28. The human body existence/non-existence sensor 27 senses existence/non-existence information of a human body, and the distance sensor 28 measures the distance information. According to this, it is possible to estimate a state of a nursing care recipient in the restroom. That is, it is possible to estimate a normal state of a nursing care recipient or an abnormal state such as falling over using the 3D sensor provided in the wireless tag 10 and/or the distance sensor 28 instead of the 3D sensor provided in the wireless tag 10.

FIG. 4(c) shows the distance information measured by the distance sensor 28. When a distance to a toilet seat is measured by the distance sensor 28, if a nursing care recipient is sitting on the toilet seat, the measured distance becomes short. Therefore, if the distance sensor 28 measures the distance to the toilet seat while the human body existence/non-existence sensor 27 is detecting a state of existence of a human body, it is possible to estimate that the human falls over.

The existence/non-existence information of a human body from the human body existence/non-existence sensor 27 and the distance information from the distance sensor 28 are used for determining a watching level by the determining means 50. The determining means 50 determines falling over from the toilet seat, and determines change of the watching level made by stay time in the restroom. The stay time in the restroom can be measured by time elapsed after the existence/non-existence information of the human body is sensed by the human body existence/non-existence sensor 27.

The output means 60 outputs a name of a nursing care recipient, and a watching level made by falling over in the restroom and stay time in the restroom.

FIG. 5 is a conceptual diagram showing communication with a care giver in the nursing care recipient watching support system of the embodiment.

A caregiver brings the wireless tag 10 which is equal to that of a nursing care recipient. Therefore, a unique identification code as a caregiver is given to the wireless tag 10 of the caregiver. A position of the caregiver is specified in the cloud system 80 by the respective received signal levels from the wireless tags 10 measured by the access points 20 which are set in a plurality of measuring positions.

Nursing care recipient information is informed from the cloud system 80 to a staff terminal 61 attached to a caregiver through the Internet.

Since the caregiver receives information from the cloud system 80 at a place even other than the facility, it is possible to check the nursing care recipient and can receive the information.

The position information of the caregiver is uploaded to the cloud system 80 and is accumulated. The accumulated position information of the caregiver in a predetermined period is processed statistically, and accumulated as trend data on a daily, weekly or monthly basis, and the position information can be utilized as behavior analysis of a caregiver and history information of caretaking behavior.

FIG. 6 is a concrete conceptual diagram for realizing the nursing care recipient watching support system of the embodiment by the cloud system.

All of attribute data obtained by a nursing care recipient are reserved and accumulated in the cloud system 80. From the big date reserved and accumulated in the cloud system 80, determination model for determining as event which fits to a specific nursing care recipient is constructed. The determination model is constructed by conducting statistical processing utilizing multivariate analysis by batch processing, and by conducting determination processing by algorithm into which an online learning method is taken. The statistically processed event data is reserved on a daily, weekly or monthly basis.

The statistically processed event data of the 3D sensor becomes determination standards in a deep sleeping state, a shallow sleeping state and an awaking state from analysis of principal component obtained by multivariable analysis after matrix data of a multivariable data value which is seize as action vector value of the sensor is normalized.

The 3D sensor includes a triaxial acceleration sensor. According to this, the triaxial acceleration sensor can determines an awaking state, a bed-in state, a shallow sleeping state, a deep sleeping state by the above-described logical value by the triaxial acceleration sensor under a condition that the nursing care recipient is in the living room of the nursing care recipient.

In the triaxial, an axis from a toe to a top of a head of a human body is an X axis, an axis from a left side surface to a right side surface of the human body is a Y axis, and an axis from a back to a belly of the human body is a Z axis.

An angle formed between the X axis and a vertical axis (upward direction in gravitational force direction) is defined by means of 0° to 90°. 0° is a state where a human body stands or sits, and 90° is a state where a human body gets lying down.

Standards of determination are determined as follows. A state where the X axis moves between 0° to 45° is the awaking state. A state where the X axis is from 45° to 90° is the bed-in state. When variation in acceleration in the Y axis and Z axis direction in the bed-in state is small, the state is determined as the deep sleeping state. When variation in acceleration in the Y axis and Z axis direction in the bed-in state exceeds a constant value, the state is determined as the shallow sleeping state.

When the state is transited from the bed-in state to the awaking state, this is determined as an awaking event. The awaking state and the bed-in state in the bed in, and a combination thereof can be determined as a bed-separating state.

For example, a state where a human body stands or sits is defined as "A", a state where the human body gets lying down is defined as "B", a state where the human body awakes is defined as "C", a state where the human body is in bed is defined as "D", a state where the human body is deeply sleeping is defined as "O", a state where the human body is shallowly sleeping is defined as "P", and an awaking event is defined as "M".

The bed-separating is defined after T1 seconds are elapsed after the "M" event passes from the "C" state, or is defined if the "C" state is transited to the "A" state after T2 seconds through the "M" event. Here, T1 and T2 are individual variables by a nursing care recipient. It is preferable that an angle to determine the "A" state is also an individual variable by the nursing care recipient.

If a bed-separating determination state is defined as "SO", "SO" determination standards and symbol strings SO1, SO2 . . . from range determination, logical determination, angle range determination or plurality of logical determination. This symbol string state is stored in chronological order together with the nursing care recipient ID.

If the above-described time series data is reserved in a storing region and the preserved time series data is displayed in a time series graph manner by the output means 60, they can be visualized and it is possible to watch the behavior history and seeping state of a nursing care recipient at night. At the same time, the time series data is displayed and visualized in a trend graph manner on a daily, weekly or monthly basis. These data sets are subjected to multivariable analysis such as analysis of principal component and independent component analysis from data matrix by batch processing after the event. An eigenvector or an eigenvalue extracted from the matrix values of these event components can specify an individual person. Variance-covariance values are obtained from these matrix values. A correlation coefficient value from the variance-covariance value can also be utilized as an important feature value.

FIG. 7 is another concrete conceptual diagram for realizing the nursing care recipient watching support system of the embodiment by the cloud system.

If the wireless tag 10 is attached to a diaper, urination in the diaper is detected as event processing of the 3D sensor by the wireless tag 10, and urination and bowel motion are detected.

In this case, the 3D sensor includes a temperature sensor for example. The determination standard is determined by time series temperature distribution. Temperature at the time of urination and temperature at the time of bowel motion are comparison distribution with respect to an initial value as individual index by a nursing care recipient. It is preferable to predict bowel motion timing, urination timing from past time series data to determine.

As event data of the 3D sensor, temperature detected from urination and moisture are detected by an analog value. Since there are various determination standards, data in which it is already text-converted by a determined method is made as an urination detection value. According to this, the determination method can be conducted at high speed and determination processing becomes easy.

To obtain an analog sample value from the event data of the 3D sensor, to predict future, statistics/learning model is formed, and an adaptive value of an individual person is predicted by model determination. To save labor of a caregiver at night, a diaper exchanging period can be made as index data for clarification, and this contributes to improvement of feeling of a caregiver himself or herself at the same time. It is possible to reduce the exchanging operation of diaper of a bedridden nursing care recipient and to reduce night operations of a caregiver from a predicted value of the exchanging timing.

If the 3D sensor includes a vital sensor, it is possible to detect heartbeat and breathing value. A temperature sensor and the vital sensor are mounted on a finger or an ear to detect pulsing motion, and the heartbeat and the breathing value are obtained from vibration wave shape. In this manner, the 3D sensor is a sensor which includes at least one of an acceleration sensor for sensing attitude of a human, a sensor for measuring environment in a facility, and a sensor for collecting and detecting biometric information of a human.

FIG. 8 are conceptual diagrams showing installation examples of the access points in the nursing care recipient watching support system of the embodiment.

As shown in FIG. 8(a), a first access point 20A is placed in each of living rooms, a second access point 20B is placed in the restroom and the bathroom, and a third access point 20C is placed in the passageway. A first antenna 21, a second antenna 22, a first wireless LSI 23, a second wireless LSI 24 and a control CPU 25 are mounted on the third access point 20C like the first access point 20A, and the third access point 20C includes a battery 26 for driving these members.

A wireless gateway 70 which conducts wireless communication with the first, access point 20A, the second access point 20B and the third access point 20C, and which is connected to an Internet router is placed in the facility.

FIG. 8(b) shows a problem concerning the access point 20A placed in the living room where a nursing care recipient sleeps.

In a wide space, after the access point 20C is placed, it is possible to obtain matching process information from correlation data with physical meeting position corresponding to that place while moving the wireless tag 10, and it is possible to estimate whereabouts.

However, as shown in FIG. 8(b), in a narrow space such as a living room, there is a problem of construction structure in a facility that penetration efficiency of electric wave is different in a body wall and a panel wall, and there is a case where there is no correlation between a received signal level detected by the access point 20A and position information due to a mounting position of the wireless tag 10 (e.g., chest side and back side).

Hence, as shown in FIG. 8(c), in a narrow space such as the living room where a nursing care recipient sleeps, the access point 20A is placed on a ceiling surface of a room, especially at a central position of the ceiling surface, a flat plate directionality (close to shower beam) capable receiving only in a room) antenna is used for directionality of a wireless tag receiving antenna used for the access point 20A.

The access point 20A is placed at the central position of the ceiling surface of the living room, and the flat plate directionality antenna is used for the wireless tag receiving antenna used for the access point 20A placed on the ceiling surface of the living room. According to this, it is possible to prevent electric wave from leaking to adjacent living room, and variation of a receiving level caused by a mounting position of the wireless tag 10 can also be solved.

If a received signal level is unexpected uncorrelated value among time series data, it is also effective to conduct position determination, to ignore the determination and to use one of past old detection signal patterns. It is also effective to assign the highest priority to compartment information together with such position determination, to change the determination standard in specific compartment information.

FIG. 9 is a cloud connection diagram with a wireless communication environment in a facility in the nursing care recipient watching support system of the embodiment, and FIG. 10 is a conceptual diagram showing understanding of a whereabouts of a nursing care recipient and its attribute information in the nursing care recipient watching support system of the embodiment.

FIG. 11 is a conceptual diagram of a nursing care recipient watching support system of another embodiment.

In this embodiment, the access point 20 includes the human body existence/non-existence sensor 27, and the human body existence/non-existence sensor 27 senses existence/non-existence information of a human body. Such can access point 20 is set in a watching region such as a place near a gateway such as a passageway in front of a front door.

In this embodiment also, communication data with respect to the wireless tag 10 is sent to the cloud system 80, the communication data is algorithm-processed by the cloud system 80, and this is output to the staff terminal 61 used by a caregiver as message through the Internet.

When a nursing care recipient enters the watching region, the staff terminal 61 outputs warning, but since the warning is output through the Internet, delay of several seconds is generated in output of the warning in some cases.

Hence, in this embodiment, human body sensing information is sent from the access point 20 to a warning output display warning lamp terminal 62, and the warning output display warning lamp terminal 62 outputs warning information. The warning information is output by a local network without through the Internet. According to this, it is possible to prevent the output from delaying.

The fact that the access point 20 sends the information to the warning output display warning lamp terminal 62 is limited to a case where the unique identification code of the wireless tag 10 determines that a person is a nursing care recipient. The fact can also be limited to a case where the individual watching level information determines that a watching level is high. It is also effective to remove a case where a caregiver exists near the nursing care recipient. It is effective to remove also a case where a degree of danger that a nursing care recipient goes out from the front door is low.

FIG. 12 are output screen image diagrams of the nursing care recipient watching support system of the present invention.

As shown in FIG. 12(a), a name of a nursing care recipient, an existing place of the nursing care recipient and a state (awaking, bed-separating, bed-in, sleeping, restroom) of the nursing care recipient are output and displayed for each of the living rooms.

Further, sleeping analysis history such as waking, shallow sleeping and deep sleeping for each of the nursing care recipients is output and displayed as shown in FIG. 12(b).

As described above, according to the embodiments, it is possible to estimate an existent position of a nursing care recipient in doors A. Therefore, it is possible to reduce a burden of a caregiver and to sufficiently handle the nursing care recipient.

INDUSTRIAL APPLICABILITY

The nursing care recipient watching support system of the present invention can be applied also to a system for very small children such as a preschool and a kindergarten.

EXPLANATION OF SYMBOLS 10, 10a wireless tag
10b wireless tag for caregiver
11 antenna
12 wireless LSI
13 control CPU
14 3D event sensor
15 battery
20 access point
20a, 20b, 20c, 20d, 20e access point
20A first access point
20B second access point
20C third access point
21 first antenna
22 second antenna
23 first wireless LSI
24 second wireless LSI
25 control CPU
26 battery
27 human body existence/non-existence sensor
28 distance sensor
30 storing means
40 position information extracting means
50 determining means
60 output means
61 staff terminal
62 warning output display warning lamp terminal
70 wireless gateway
80 cloud system
P measuring position
P0101, P0102, P0201, P1607, P1707, P1907, P1909 measuring position
A indoor

The invention claimed is:

1. A nursing care recipient watching support system comprising
wireless tags attached to nursing care recipients;
a plurality of access points located at predetermined indoor locations;
storing means in which the access points are located at the predetermined locations, received signal levels of the wireless tags at the access points are previously measured at a plurality of arbitrary measuring positions, and the measured received signal levels are stored in the storing means as position estimating signal level patterns together with position information of the measuring positions; and
position information extracting means which detects the received signal levels at the access points from the wireless tags, which handles the detected received signal levels as detection signal level patterns, which selects the position estimating signal level pattern which is the closest to the detection signal level pattern, and which extracts the position information of the selected position estimating signal level pattern;
in which
an existent position of the indoor nursing care recipient is estimated from the position information extracted by the position information extracting means, and watching of the nursing care recipient is supported, wherein
the position information, indoor compartment attribute information including at least one of a living room, a share room, a conversation room, a kitchen, a bathroom and an entrance with respect to the measuring position, and watching level information corresponding to the indoor compartment attribute information are stored in the storing means,
the position information extracting means extracts the position information, the indoor compartment attribute information and the watching level information, and
output means outputs the position information, the indoor compartment attribute information and the watching level information.

2. The nursing care recipient watching support system according to claim 1, further comprising determining means which estimates a moving direction of the nursing care recipient from the time series position information during continuation of extraction of the same indoor compartment attribute information, and determines a watching level from the estimated moving direction, wherein
when the determining means determines the watching level which is different from the watching level information, the output means outputs the watching level instead of the watching level information.

3. The nursing care recipient watching support system according to claim 1, wherein the wireless tag includes sending interval changing means for changing sending interval of a sending signal, and
the wireless tag changes the sending interval in accordance with the indoor compartment attribute information extracted by the position information extracting means, and sends the sending signal.

4. The nursing care recipient watching support system according to claim 1, wherein watching level changing information corresponding to time zone is stored in the storing means, and
the output means outputs the watching level information which is changed by the watching level changing information.

5. The nursing care recipient watching support system according to claim 1, wherein the wireless tag includes a 3D sensor, and
the wireless tag outputs a detection value by the 3D sensor as a sending signal.

6. The nursing care recipient watching support system according to claim 1, wherein a unique identification code is given to the wireless tag,
nursing care recipient identification information corresponding to the unique identification code and individual watching level information which is set corresponding to the nursing care recipient identification information are stored in the storing means, and
if the individual watching level information is a watching non-required level or a watching low level, the output means outputs the watching non-required level or the watching low level even if the watching level information is a watching-required level or a watching high level.

7. The nursing care recipient watching support system according to claim 1, wherein the wireless tag includes a caregiver wireless tag attached to a caregiver who gives care to the nursing care recipient,
the position information extracting means extracts the position information of the nursing care recipient and position information of the caregiver,
the nursing care recipient watching support system further includes determining means for determining a watching level from the position information of the nursing care recipient and the position information of the caregiver extracted by the position information extracting means when the caregiver does not exists in a predetermined range of the nursing care recipient, and
the output means outputs a determination result and the position information when the determining means determines a watching-required level.

8. The nursing care recipient watching support system according to claim 1, wherein the access point includes a human body existence/non-existence sensor and a distance sensor, and
an human body existence/non-existence information which is sensed by the human body existence/non-existence sensor and distance information which is measured by the distance sensor are sent from the access point.

9. The nursing care recipient watching support system according to claim 8, wherein the access point including the human body existence/non-existence sensor and the distance sensor is placed in a restroom,
motion to the restroom is estimated by position estimation made by the wireless tag, the human body existence/non-existence sensor senses timing of movement into and out from the restroom, and
the distance sensor senses a motionlessness state in the restroom.

10. The nursing care recipient watching support system according to claim 5, wherein the 3D sensor includes a triaxial acceleration sensor,
and the triaxial acceleration sensor determines an awaking state, bed-in state, a shallow sleeping state and a deep sleeping state under a condition that the nursing care recipient is located in the living room of the nursing care recipient.

11. The nursing care recipient watching support system according to claim 1, wherein in the living room where the nursing care recipient sleeps,
the access point is placed at a central position of a ceiling surface of the living room, and
a flat plate directionality antenna is used as a wireless tag receiving antenna used for the access point located on the ceiling surface of the living room.

12. The nursing care recipient watching support system according to claim 1, wherein the access point includes a human body existence/non-existence sensor, human body existence/non-existence information sensed by the human body existence/non-existence sensor is sent from the access point to a cloud system, and the human body existence/non-existence information is sent to a warning output display warning lamp terminal separately from the cloud system.

* * * * *